US006514960B1

(12) United States Patent
Tsai et al.

(10) Patent No.: US 6,514,960 B1
(45) Date of Patent: Feb. 4, 2003

(54) USE OF BISMUTH SUBGALLATE IN INHIBITION OF PRODUCTION OF NITRIC OXIDE SYNTHASE

(75) Inventors: Ying-Chieh Tsai, Taipei (TW); Szu-Hui Wu, Taipei (TW); Cheng-Sheng Hsu, Taipei (TW)

(73) Assignee: Hedonist Biochemical Technologies Co., Ltd., Taipei (TW)

( * ) Notice: Subject to any disclaimer, the term of this patent is extended or adjusted under 35 U.S.C. 154(b) by 74 days.

(21) Appl. No.: 09/940,405

(22) Filed: Aug. 27, 2001

(51) Int. Cl.[7] ..................... A61K 31/555; A61K 31/045
(52) U.S. Cl. ........................ 514/186; 514/729
(58) Field of Search ................ 514/186, 503, 514/729

(56) References Cited

U.S. PATENT DOCUMENTS

| | | | |
|---|---|---|---|
| 6,030,985 A | 2/2000 | Gentile et al. | 514/307 |
| 6,071,906 A | 6/2000 | Hansen et al. | 514/227.2 |
| 6,232,341 B1 | 5/2001 | Chen et al. | 514/503 |
| 6,235,747 B1 | 5/2001 | Lowe, III et al. | 514/278 |
| 6,133,306 A1 | 10/2001 | Beal | 514/418 |

FOREIGN PATENT DOCUMENTS

JP   2000095681   *   4/2000

OTHER PUBLICATIONS

The Merck Index (12th edition) p. 213 (1996).*
Millington, et al., "Effective Treatment Strategies for Diabetic Foot Wounds", *The Journal of Family Practice*, vol. 49(11) Supplement, pp S40–S48, Nov., 2000.

Sumpio, "Primary Care: Foot Ulcers", *The New England Journal of Medicine*, vol. 343(11), pp. 787–793, Sep. 14, 2000.

Cochran et al., "Insights into the Role of Nitric Oxide in Inflammatory Arthritis" *Medical Research Reviews*, vol. 16, No. 6, pp. 547–563 (1996).

Mulligan et al., "Tissue Injury Caused by Deposition of Immune Complexes is L–arginine Dependent" *Proc. Natl. Acad. Sci. USA*, vol. 88, pp. 6338–6342. Jul. 1991.

Pfeilschifter et al., "Therapeutic Strategies for the Inhibition of Inducible Nitric Oxide Synthase–Potential for a Novel Class of Anti–Inflammatory Agents" *Cell Biology International*, vol. 20, No. 1, 51–58 (1996).

Hobbs et al. "Inhibition of Nitric Oxide Synthase as a Potential Therapeutic Target" *Annual Review Pharmacol. Toxicol 39*: 191–220 (1999).

Moncada et al. "The L–Arginine–Nitric oxide Pathway" *The New England Journal of Medicine*, Dec. 30, 1993.

* cited by examiner

Primary Examiner—Phyllis G. Spivack
(74) Attorney, Agent, or Firm—Merchant & Gould P.C.

(57) ABSTRACT

The present invention discloses the use of bismuth subgallate in the inhibition of the production of nitric acid synthase. Also disclosed is the synergistic efficacy of bismuth subgallate in combination with borneol in the inhibition of the production of nitric acid synthase.

21 Claims, 3 Drawing Sheets

USE OF BISMUTH SUBGALLATE IN INHIBITION OF PRODUCTION OF NITRIC OXIDE SYNTHASE

BACKGROUND OF THE INVENTION

1. Field of the Invention

The present invention relates to a new use of bismuth subgallate in the inhibition of the production of nitric acid synthase.

2. Description of the Prior Art

Nitric oxide (NO) is an unstable free radical that mediates both homeostatic and pathophysiologic processes within the cardiopulmonary, nervous, and immune systems. The list of potential disease associations for NO is increasing dramatically (Cochran et al., *Medicinal Research Reviews*, 1996, 16(6):547–563). Thus, agents that modulate the activity of NO may be of considerable therapeutic value. In particular, those that reduce the formation of NO may be beneficial in pathophysiological states in which excessive production of NO is a contributory factor. These include diseases such as septic shock, neurodegenerative disorders, and inflammation. NO is formed endogenously by a family of enzymes known as nitric oxide synthases (NOS) (Hobbs et al., *Annu. Rev. Pharmacol. Toxicol*, 1999, 39:191–220).

It is known that three distinct isoforms of NOS have been identified: an inducible form (iNOS) and two constitutive forms referred to neuronal NOS (nNOS) and endothelial NOS (eNOS). The NOS, particularly iNOS, are associated with the conditions including platelet aggregation, homeostatic processes, tissue injury, inflammatory conditions, shock states, immune disorders, disorders of gastrointestinal motility and diseases of the central nervous system (Epstein, The New England Journal of Medicine, 1993, 329(27): 2002–2011; Hobbs. et al, Annu. Rev. Pharmacol. Toxicol., 1999, 39: 191–220; Pfeilschfter et al., Cell Biology International, 1996, 20(1): 51–58). The NOS are also associated with the conditions caused by nitric oxide, such as tissue injury, cerebral ischemia, epilepsy, immunity and inflammation (Mulligan et al., Proc. Natl. Acad. Sci. USA, 1991, 88:6338–6342).

Given the above, it is expected that the compounds or agents capable of decreasing the amount or activity of NOS are useful as therapeutic agents. For example, U.S. Pat. No. 6,030,985 discloses the amidine derivatives useful for treating and preventing conditions in which inhibition of nitric oxide synthase is beneficial, such as stroke, schizophrenia, anxiety, and pain. U.S. Pat. No. 6,071,906 provides a pharmaceutical compositions containing an amidino derivative useful as an inhibitor of nitric oxide synthase. U.S. Pat. No. 6,133,306 features treating a neurodegenerative disease by administration of an effective amount of a nitroindazole, which is an inhibitor of neuronal nitric oxide synthase. U.S. Pat. No. 6,235,747 relates to certain 6-phenyl-pyridin-2-ylamine derivatives that exhibit activity as nitric oxide synthase (NOS) inhibitors, to pharmaceutical compositions containing them and to their use in the treatment and prevention of central nervous system disorders.

Bismuth subgallate is the product of the reaction among gallic acid, glacial acetic acid and bismuth nitrate which is represented by a molecular formula of $C_7H_5BiO_6$. It is known as an oral anti-diarrhea agent effective in treating acute or chronic diarrhea by virtue that it can react with H2S, which is present in large quantities in the intestinal tract due to abnormal fermentation, and thereby alleviate diarrhea and pains caused by gas irritation to the intestinal tract. Bismuth subgallate can also be used as a disinfectant in view of its nature as a benzene derivative.

A pharmaceutical composition for wound healing comprising bismuth subgallate and borneol is disclosed in U.S. Pat. No. 6,232,341. However, none of the prior art teaches or suggests the new use of bismuth subgallate in the inhibition of NO synthase.

SUMMARY OF THE INVENTION

It is surprisingly found that bismuth subgallate is useful in the inhibition of the production of nitric oxide synthase (NOS).

Accordingly, the invention provides the new use of bismuth subgallate in the inhibition of the production of NOS.

An object is to provide a method of inhibiting the production of nitric oxide synthases (NOS) in a subject, comprising administering to said subject in need thereof an effective amount of bismuth subgallate; wherein said bismuth subgallate is administered in an amount effective to inhibit the production of NOS. According to the preferred embodiment of the invention, the method comprises administering to said subject in need thereof an effective amount of bismuth subgallate in combination with borneol, wherein said bismuth subgallate in combination with borneol are administered in an amount synergistically effective to inhibit the production of NOS.

Another objective of the invention is to provide a pharmaceutical composition for inhibiting the production of nitric oxide synthases comprising an effective amount of bismuth subgallate sufficient to inhibit the production of NOS and a pharmaceutical acceptable carrier. According to a preferred embodiment of the invention, the pharmaceutical composition of the invention further comprises borneol to provide a synergistic effect in the inhibition of the production of NOS.

DETAILED DESCRIPTION OF THE INVENTION

Figure 1:
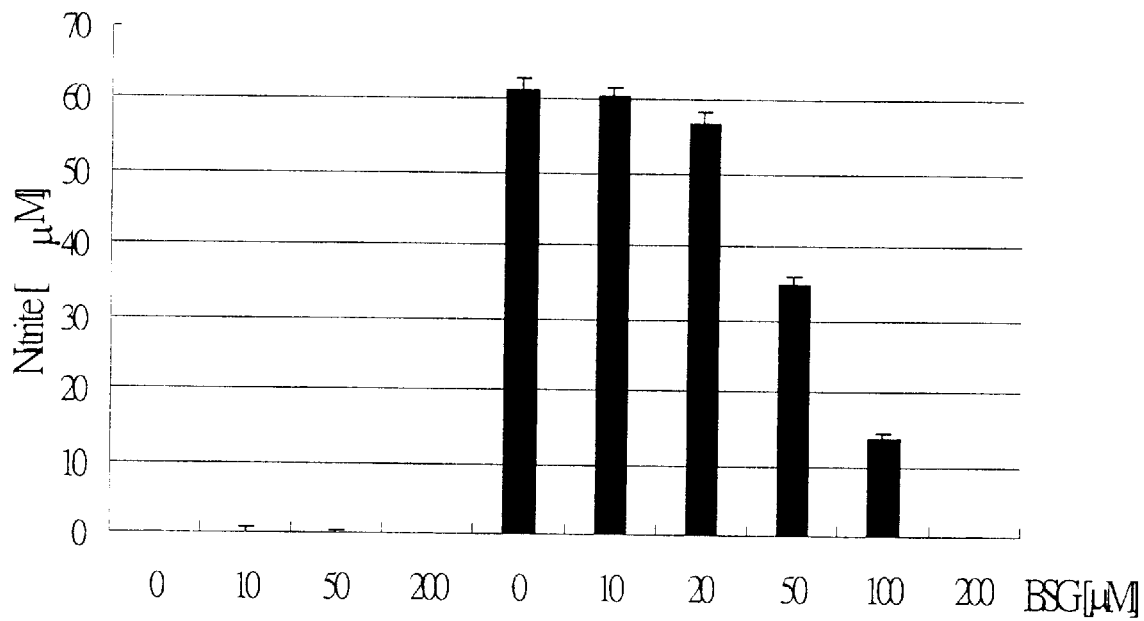
FIG. 1 shows the effect of bismuth subgallate on NO production by the activated RAW 264.7 cells.

The present invention relates to a new use of bismuth subgallate in the inhibition of the production of nitric oxide synthases. It is surprisingly found in the invention that bismuth subgallate is useful in the inhibition of the production of nitric oxide synthase. In particular, the claimed invention provides a method of inhibiting the production of nitric oxide synthases (NOS) in a subject, comprising administering to said subject in need thereof an effective amount of bismuth subgallate, wherein said bismuth subgallate is administered in an amount effective to inhibit the production of NOS. In addition, it is found that bismuth subgallate in combination with borneol exhibit a synergistic effect in the inhibition of the production of nitric oxide synthase. In particular, the claimed invention provides a method of inhibiting the production of nitric oxide synthases (NOS) in a subject, comprising administering to said subject in need thereof an synergistically effective amount of bismuth subgallate in combination with borneol, wherein said bismuth subgallate in combination with borneol are administered in an amount synergistically effective to inhibit the production of NOS.

Definition

The term "bismuth subgallate" as used herein, refers to the product of the reaction among gallic acid, glacial acetic acid and bismuth nitrate which is represented by a molecular formula of $C_7H_5BiO_6$.

The term "effective amount" as used herein refers to an amount sufficient to provide an effect sufficient for the inhibition of the production of nitric oxide synthases to bring improvement in patients.

The term "carrier" as used herein refers to a diluent, an excipient, a recipient and the like for use in preparing admixtures of a pharmaceutical composition.

Pharmaceutical Composition

The invention provides a pharmaceutical composition for use in the inhibition of the production of nitric oxide synthase, which comprises an effective amount of bismuth subgallate sufficient to inhibit the production of NOS and a pharmaceutical acceptable carrier.

The pharmaceutical composition preferably comprises bismuth subgallate at an amount ranging from 0.05 to 40 percent by weight. More preferably, the amount of bismuth subgallate in the pharmaceutical composition according to the present invention is from 1 to 20 percent by weight. Most preferably, the amount of bismuth subgallate in the topical pharmaceutical composition according to the present invention is from 2 to 10 percent by weight.

According to the invention, the pharmaceutical composition further comprising borneol is synergistically effective in the inhibition of nitric oxide synthases. Preferably, the pharmaceutical composition comprises bismuth subgallate at an amount ranging from 1 to 30 percent by weight and borneol at an amount ranging from 0.05 to 10 percent by weight. More preferably, the amounts of bismuth subgallate and borneol in the pharmaceutical composition are from 3 to 15 percent by weight, and from 0.1 to 5 percent by weight, respectively. Most preferably, the amounts of bismuth subgallate and borneol in the pharmaceutical composition are from 4 to 8 percent by weight and from 0.5 to 1 percent by weight, respectively.

Apart from the above-mentioned active ingredients, the pharmaceutical composition according to the present invention may further comprise other traditional agents which are helpful in the inhibition of nitric oxide synthases, such as the compounds disclosed in WO 94/12165, WO 94/14780, WO 93/13055, EP 0446699A1, U.S. Pat. Nos. 5,132,453, 6,030,985, 6,071,906, 6,133,306 and 6,235,747. The incorporation of these traditional agents into the pharmaceutical composition according to the present invention is readily available for ordinary persons skilled in the art.

According to the invention, suitable doses of the pharmaceutical composition according to the invention may be determined routinely by the medical practitioner or other skilled persons, and include the respective doses discussed in the prior art disclosing bismuth subgallate and borneol that are mentioned hereinbefore. The disclosures of which are hereby incorporated by reference.

In any event, a physician, or a skilled person, will be able to determine the actual dosage which will be most suitable for an individual patient. The dosage is likely to vary depending on the condition that is to be treated, as well as the age, weight sex and response of the particular patient to be treated.

According to the invention, the pharmaceutical composition can be formulated for topical, oral, parenteral or other mode of administration. Suitable pharmaceutical carriers used in the pharmaceutical composition of the invention include, but are not limited to, water, salt solutions, alcohols, polyethylene glycols, gelatin, carbohydrates (such as lactose, amylose or starch), magnesium stearate, talc, silicic acid, viscous paraffin, fatty acid esters, hydroxymethylcellulose, polyvinyl pyrrolidone, etc.

Injectable, sterile solutions, preferably oily or aqueous solutions, as well as suspensions, emulsions, or implants, including suppositories are particularly suitable for parenteral application. Ampoules are convenient unit dosages. Oral applications are preferably administered in the forms of capsules, tablets and/or liquid formulations.

For topical applications, the pharmaceutical composition of the invention is preferably administered in the forms of paste, cream and gel paste etc. More preferably, the pharmaceutical composition may further comprise anti-inflammatory agents, astringents, emollients or analgesics.

Utility

According to the invention, the pharmaceutical composition can be used in the inhibition of the production of nitric oxide synthase. Therefore, the pharmaceutical composition is effective in the treatment of the conditions in associated with the NO synthase, such as platelet aggregation deficiency, homeostatic process disorder, tissue injury, migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, dilated cardiomyopathy, acute spinal cord injury, Huntington's disease, Parkinson's disease, glaucoma, macular degeneration, diabetic neuropathy, diabetic ulcers and cancer in a mammal, including a human.

More preferably, the pharmaceutical composition of the invention is useful in treating the conditions associated with platelet aggregation, homeostatic processes and tissue injury.

The following examples further illustrate the present invention, but are not intended to limit the scope of the present invention. The modifications and substitutions known to those skilled in the art are still within the scope and spirit of the present invention.

EXAMPLES

EXAMPLE 1

Effect of Bismuth Subgallate on Production of Nitric Oxide

The cells of the mice macrophage cell line RAW 264.7 (under accession number CCRC 60001), which was obtained from Cell Culture Research Center, Food Industry Research and Development Institute, Hsinchu, Taiwan, R.O.C., were used for the test.

The RAW 264.7 cells were incubated in a 96 well tissue culture plate (Falcon). After 24 hours, the cells were activated with Dulbecco's Modified Eagle Medium (DMEM, 2014, GibcoBRL) in the presence and absence of 100 ng/ml LPS, 100 U/ml IFN-γ and various concentrations (10 $\mu$M, 20 $\mu$M, 50 $\mu$M, 100 $\mu$M and 200 $\mu$M) of bismuth subgallate (Hwang et al., 1994, J. Biol. Chem. 269, p. 711–715). After 24 hours, 50 $\mu$l of the supernatant from each well was assayed for the presence of nitrite through the Saville modification of the Griess reaction (Green et al., Analytical Biochem, 1982, 126:131–138). The results were represented by the means plus standard errors values (Mean±SE) of three repetitions.

As shown in FIG. 1, the cells, which were not activated, by LPS and IFN-γ did not produce NO. In contrast, the cells, which were activated, by LPS and IFN-γ produced up to 65 $\mu$M of NO. Furthermore, those from cells incubated in the presence of bismuth subgallate showed a reduction in nitrite concentration, reflecting the reduction in NO production. The production of NO was inversely proportional to the increase in the concentration of bismuth subgallate.

EXAMPLE 2
Effect of Borneol on Production of NO

Figure 2:
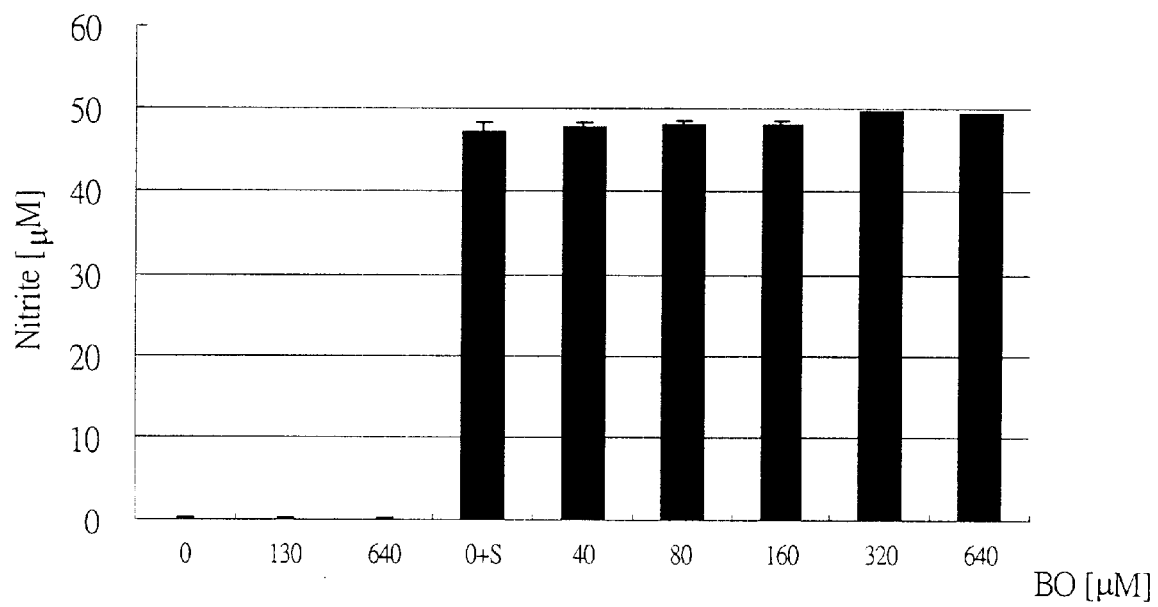
FIG. 2 shows the effect of borneol on NO production by the activated RAW 264.7 cells.

The effect of borneol on the inhibition of NO synthase was tested through the same experimental procedures as described in Example 1. Various concentrations of borneol (0 $\mu$M, 40 $\mu$M, 80 $\mu$M, 160 $\mu$M, 320 $\mu$M and 640 $\mu$M) were used to replace bismuth subgallate of Example 1. As shown in FIG. 2, the results were represented by the means plus standard errors values (mean±SE) of three repetitions. The production of NO was not significantly inhibited by the borneol.

Figure 3:
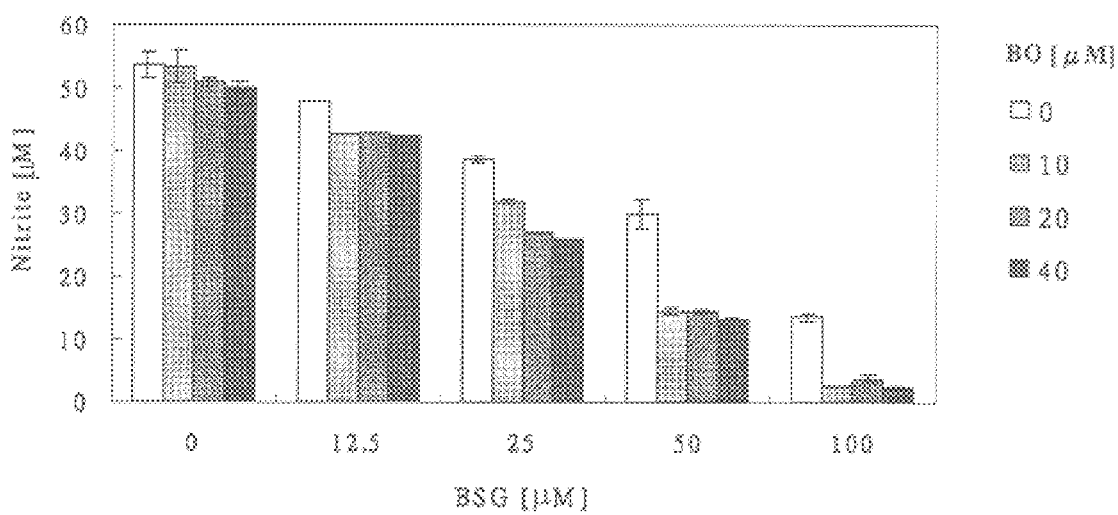
FIG. 3 shows the effect of bismuth subgallate in combination with borneol on NO production by the activated RAW 264.7 cells.

EXAMPLE 3
Synergistic Effect of Bismuth Subgallate in Combination with Borneol on Production of NO The effect of bismuth subgallate in combination with borneol on the inhibition of NO synthase was tested through the similar experimental procedures as described in Example 1. The following concentrations of Bismuth subgallate: 0 $\mu$M, 12.5 $\mu$M, 25 $\mu$M, 50 $\mu$M and 100 $\mu$M, were combined with the following concentrations of borneol: 0 $\mu$M, 10 $\mu$M, 20 $\mu$M and 40 $\mu$M, respectively, to obtain the combinations for the replacement of bismuth subgallate used in Example 1. The results were represented by the mean values of three repetitions with standard errors (Mean±SE). As shown in FIG. 3, the production of NO was significantly lowered by the treatment of the combination of bismuth subgallate with borneol. The effect of the combinations on the production of NO was more significant than that of bismuth subgallate only. In other words, a combination of bismuth subgallat with borneol exhibits a synergistic effect on inhibiting NO synthase.

What is claimed is:

1. A method of inhibiting the production of nitric oxide synthases (NOS) in a subject, comprising administering to said subject in need thereof an effective amount of bismuth subgallate, wherein said bismuth subgallate is administered in an amount effective to inhibit the production of NOS.

2. A method of claim 1, comprising administering to said subject in need thereof an synergistically effective amount of bismuth subgallate in combination with borneol, wherein said bismuth subgallate in combination with borneol are administered in an amount synergistically effective to inhibit the production of NOS.

3. A synergistic pharmaceutical composition for inhibiting the production of NOS, the composition consisting essentially of bismuth subgallate and borneol in amounts sufficient to inhibit the production of NOS, the composition further comprising a pharmaceutical acceptable carrier.

4. The synergistic pharmaceutical composition of claim 3, wherein the amount of bismuth subgallate is from 0.05 to 40 percent by weight bismuth.

5. The synergistic pharmaceutical composition of claim 4, wherein the amount of bismuth subgallate is from 1 to 20 percent by weight.

6. The synergistic pharmaceutical composition of claim 5, wherein the amount of bismuth subgallate is from 2 to 10 percent by weight.

7. The synergistic pharmaceutical composition of claim 3, wherein the amount of bismuth subgallate and borneol range from 1 to 30 percent by weight and from 0.05 to 10 percent by weight, respectively.

8. The synergistic pharmaceutical composition of claim 7, wherein the amount of bismuth subgallate and borneol range from 3 to 15 percent by weight and front 0.1 to 5 percent by weight, respectively.

9. The synergistic pharmaceutical composition of claim 8, wherein the amount of bismuth subgallate and borneol range from 4 to 8 percent by weight and from 0.5 to 1 percent by weight, respectively.

10. The synergistic pharmaceutical composition of claim 3, further comprising another NOS inhibitor.

11. The synergistic pharmaceutical composition of claim 3, further comprising another NOS inhibitor.

12. The synergistic pharmaceutical composition of claim 3, which is administered in topical, oral or parenteral route.

13. The synergistic pharmaceutical composition of claim 3, which is administered in topical, oral or parenteral route.

14. A method of treating a disease in a subject in which nitric oxide production is implicated, comprising administering to said subject in need thereof an effective amount of bismuth subgallate, wherein said bismuth subgallate is administered in an amount effective to inhibit the production of NOS.

15. The method of claim 14, further comprising administering borneol in an amount that is synergistically effective in combination with said bismuth subgallate.

16. The method of claim 14, wherein the condition is platelet aggregation deficiency.

17. The method of claim 14, wherein the condition is homeostatic process disorder.

18. The method of claim 14, wherein the condition is tissue injury.

19. The method of claim 14, wherein the condition is inflammatory disease.

20. The method of claim 14, wherein the inflammatory disease is asthma.

21. The method of claim 14, wherein the disease is selected from the group consisting of platelet aggregation deficiency, homeostatic process disorder, tissue injury, migraine, inflammatory diseases, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions, emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, dilated cardiomyopathy, acute spinal cord injury, Huntington's disease, Parkinson's disease, glaucoma, macular degeneration, diabetic neuropathy, diabetic ulcer and cancer.

* * * * *

UNITED STATES PATENT AND TRADEMARK OFFICE
CERTIFICATE OF CORRECTION

PATENT NO. : 6,514,960 B1
DATED : February 4, 2003
INVENTOR(S) : Ying-Chieh Tsai et al.

It is certified that error appears in the above-identified patent and that said Letters Patent is hereby corrected as shown below:

Column 1,
Line 30, "The NOS," should read -- The NOSs, --
Line 38, "The NOS" should read -- The NOSs --
Line 64, "H2S" should read -- $H_2S$ --

Column 3,
Line 9, please insert a new paragraph as follows:
-- The term "borneol" as used herein, refers to the product isolated from Dryobalanops aromatica or the like and represented by the molecular formula $C_{10}H_{17}OH$. --

Column 5,
Line 43, "subgallat" should read -- subgallate --
Line 65, pleae delete the word "bismuth"

Column 6,
Lines 21-23, please delete claim 11.
Line 24, "12." should be renumbered to read -- 11. --
Line 26, please delete claim 13.
Line 28, "14." should be renumbered to read -- 12. --
Line 34, "15." should be renumbered to read -- 13. --
Lines 34, 37, 39 and 41, "The method of claim 14," should read -- The method of claim 12, --
Line 37, "16." should be renumbered to read -- 14. --
Line 39, "17." should be renumbered to read -- 15. --
Line 41, "18." should be renumbered to read -- 16. --
Line 43, "19." should be renumbered to read -- 17. --
Lines 43, 45 and 47, "The method of 14," should read -- The method of claim 12, --
Line 45, "20." should be renumbered to read -- 18. --

UNITED STATES PATENT AND TRADEMARK OFFICE
CERTIFICATE OF CORRECTION

PATENT NO. : 6,514,960 B1
DATED : February 4, 2003
INVENTOR(S) : Ying-Chieh Tsai et al.

It is certified that error appears in the above-identified patent and that said Letters Patent is hereby corrected as shown below:

Column 6 (cont'd),
Line 47, "21." should be renumbered to read -- 19. --

Signed and Sealed this

Ninth Day of September, 2003

JAMES E. ROGAN
*Director of the United States Patent and Trademark Office*